(12) United States Patent
Cogley

(10) Patent No.: US 10,729,374 B1
(45) Date of Patent: Aug. 4, 2020

(54) SLEEP SECURITY METHOD

(71) Applicant: Thomas Paul Cogley, Pinellas Park, FL (US)

(72) Inventor: Thomas Paul Cogley, Pinellas Park, FL (US)

(*) Notice: Subject to any disclaimer, the term of this patent is extended or adjusted under 35 U.S.C. 154(b) by 0 days.

(21) Appl. No.: 16/153,322

(22) Filed: Oct. 5, 2018

Related U.S. Application Data

(63) Continuation-in-part of application No. 14/996,857, filed on Jan. 15, 2016, now Pat. No. 10,091,980, which is a continuation-in-part of application No. 14/731,884, filed on Jun. 5, 2015, now Pat. No. 10,021,871.

(51) Int. Cl.
*G08B 23/00* (2006.01)
*A61B 5/00* (2006.01)
*A01M 1/10* (2006.01)
*A01M 1/02* (2006.01)
*A61M 21/00* (2006.01)

(52) U.S. Cl.
CPC ........... *A61B 5/4812* (2013.01); *A01M 1/103* (2013.01); *A61B 5/4809* (2013.01); *A61B 5/4815* (2013.01); *A01M 1/026* (2013.01); *A61B 5/0004* (2013.01); *A61B 5/486* (2013.01); *A61M 21/00* (2013.01)

(58) Field of Classification Search
CPC .............................. A61B 5/4812; A01M 1/14

USPC ............ 340/573.1, 540, 541; 600/301, 587; 43/114, 123, 132.1
See application file for complete search history.

(56) References Cited

U.S. PATENT DOCUMENTS

| | | | | |
|---|---|---|---|---|
| 5,912,624 | A * | 6/1999 | Howard, II | G08B 21/02 340/521 |
| 2007/0044372 | A1* | 3/2007 | Lang | A01M 1/023 43/114 |
| 2009/0223115 | A1* | 9/2009 | Lang | A01M 1/14 43/114 |
| 2012/0110893 | A1* | 5/2012 | Fabry | A01M 1/026 43/114 |
| 2013/0219771 | A1* | 8/2013 | Black | A01M 1/02 43/114 |
| 2015/0196766 | A1* | 7/2015 | Rosenberg | A61N 1/36139 607/42 |
| 2016/0015315 | A1* | 1/2016 | Auphan | A61B 5/4815 600/301 |
| 2017/0142953 | A1* | 5/2017 | Carver | A01M 1/026 |

* cited by examiner

*Primary Examiner* — Tai T Nguyen

(57) ABSTRACT

A sleep security method comprises the steps of providing a bed; providing at least one sensor for the detecting of a sleeping condition and for generating a signal in response to such detecting, the at least one sensor being located in operative proximity to the bed; providing a printer; providing a transceiver; operatively coupling the at least one sensor to the printer through the transceiver; and creating a written record by the printer of the detecting of the sleeping condition.

4 Claims, 7 Drawing Sheets

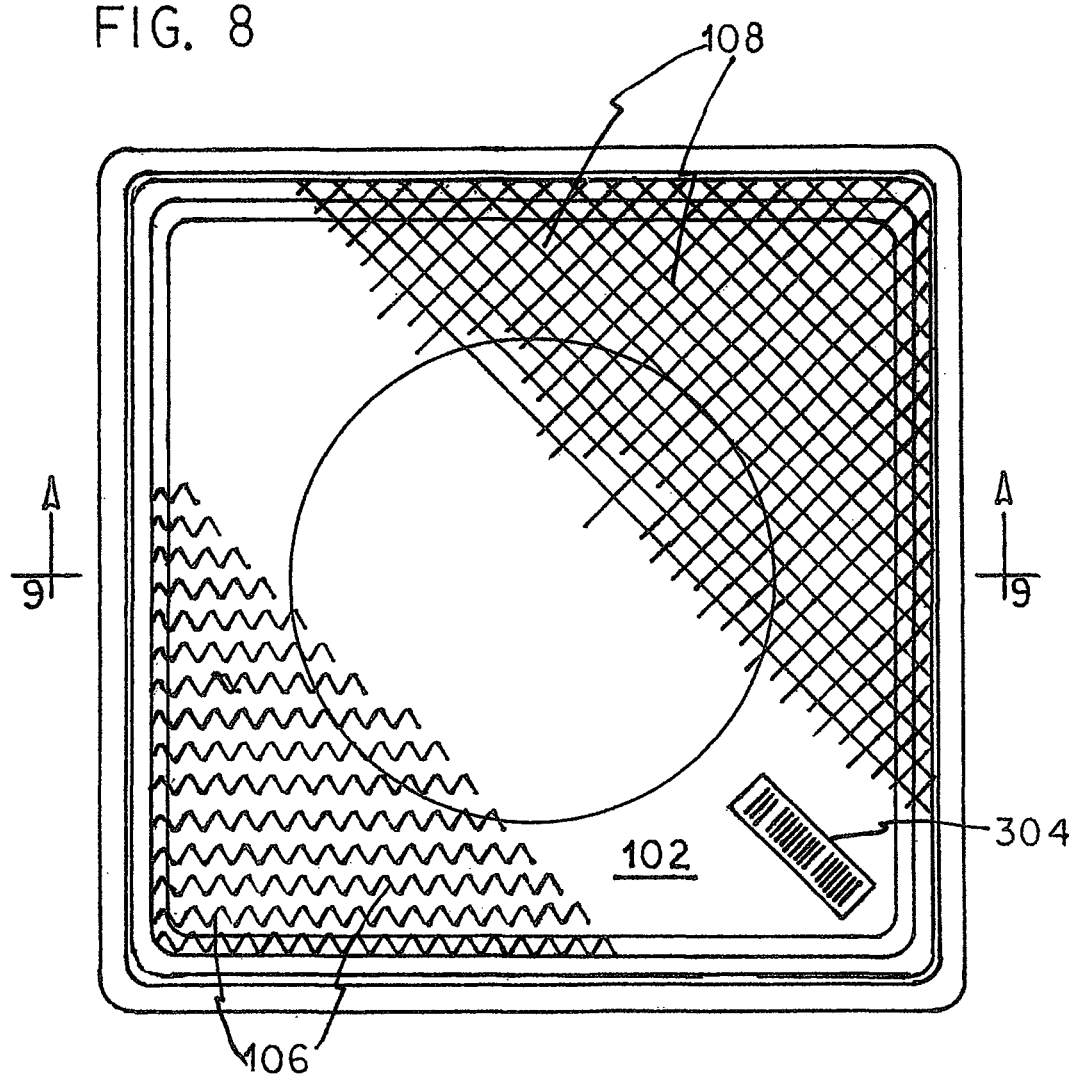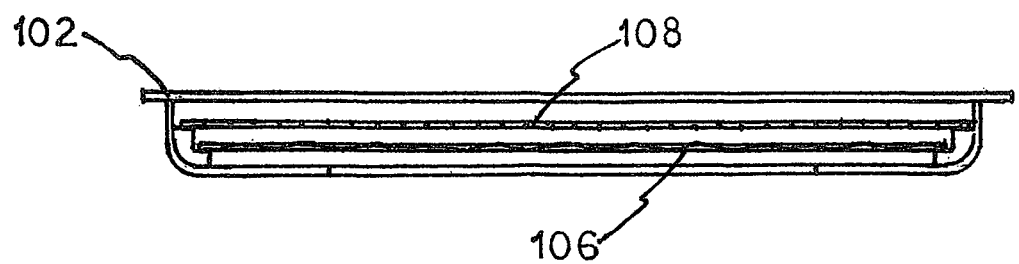

SLEEP SECURITY METHOD

RELATED APPLICATION

The present application is a continuation-in-part of pending application Ser. No. 14/996,857 filed Jan. 15, 2016 entitled "Bed Bug Detector System" issuing Oct. 9, 2018 as U.S. Pat. No. 10,091,980 which is, in turn, a continuation-in-part of Ser. No. 14/731,884 filed Jun. 5, 2015 entitled "Mobile Insect Killing System" issued Jul. 17, 2018 as U.S. Pat. No. 10,021,871, the subject matter of which applications is incorporated herein by reference.

BACKGROUND OF THE INVENTION

Field of the Invention

The present invention relates to a sleep security method and more particularly pertains to attracting bed bugs and for killing the attracted bed bugs, the attracting and killing being done in a safe, ecological, convenient, and economical manner.

SUMMARY OF THE INVENTION

In view of the disadvantages inherent in the known types of insect eliminating devices now present in the prior art, the present invention provides an improved sleep security method. As such, the general purpose of the present invention, which will be described subsequently in greater detail, is to provide a new and improved sleep security method for detecting favorable and unfavorable sleeping conditions and for printing out a record of such detecting. The detecting and the printing out are done in a safe, convenient, and economical manner. The method having all the advantages of the prior art and none of the disadvantages.

From a broad viewpoint, the present invention is a sleep security method. The first step of the sleep security method is providing a bed. The next step is providing at least one sensor for the detecting of a sleeping condition and for generating a signal in response to such detecting. The at least one sensor is located in operative proximity to the bed. The next step is providing a printer. The next step is providing a transceiver. The next step is operatively coupling the at least one sensor to the printer through the transceiver. The final step is creating a written record by the printer of the detecting of the sleeping condition.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions and method steps insofar as they do not depart from the spirit and scope of the present invention.

It is therefore an object of the present invention to provide a new and improved sleep security method which has all of the advantages of the prior art sleep security methods and none of the disadvantages.

It is another object of the present invention to provide a new and improved sleep security method which may be easily and efficiently manufactured and marketed.

It is a further object of the present invention to provide a new and improved sleep security method which is durable and reliable in construction.

An even further object of the present invention is to provide a new and improved sleep security method which is susceptible of a low cost of manufacture with regard to both materials and labor, and which accordingly is then susceptible of low prices of sale to the consuming public, thereby making such sleep security method economically available to the buying public.

Lastly, another object of the present invention is to provide a sleep security method for detecting favorable and unfavorable sleeping conditions and for printing out a record of such detecting. The detecting and the printing out are done in a safe, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 8 is a plan view of the upper pan taken along line 8-8 of FIG. 5.

FIG. 9 is a cross sectional view taken along line 9-9 of FIG. 8.

The same reference numerals refer to the same parts throughout the various Figures.

DESCRIPTION OF THE PREFERRED EMBODIMENT

Figure 1:
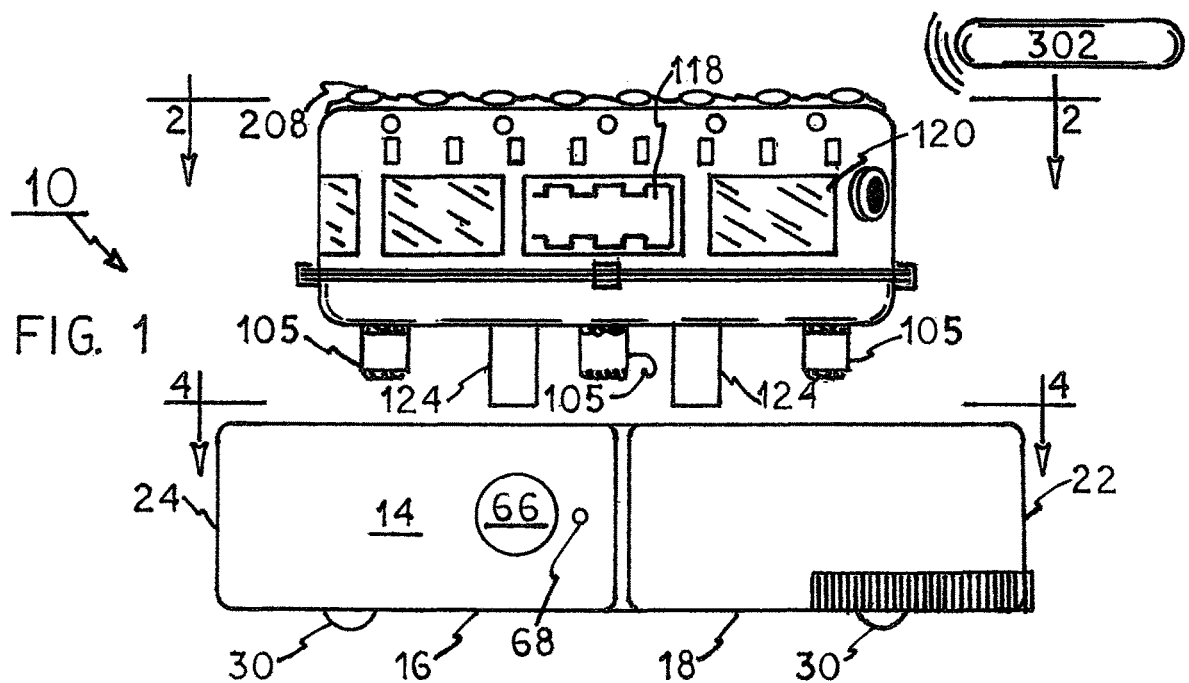
FIG. 1 is a right side elevational view of a bed bug detector system constructed in accordance with the principles of the present invention.
Figure 2:
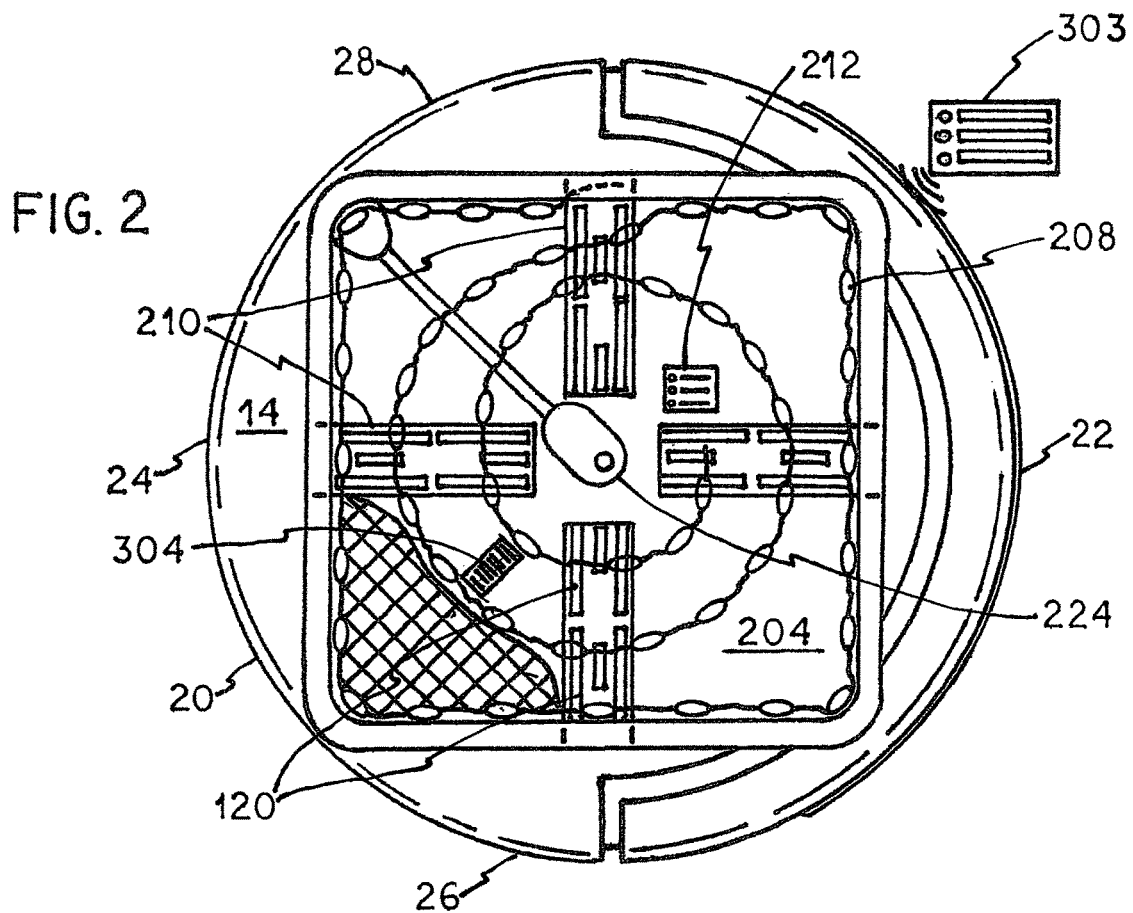
FIG. 2 is a plan view of the system taken along line 2-2 of FIG. 1.
Figure 3:
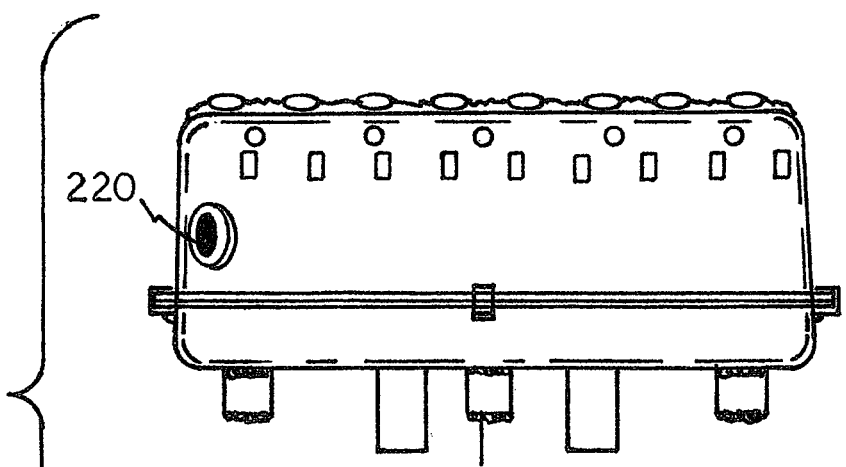
FIG. 3 is a left side elevational view of the system.
Figure 4A:
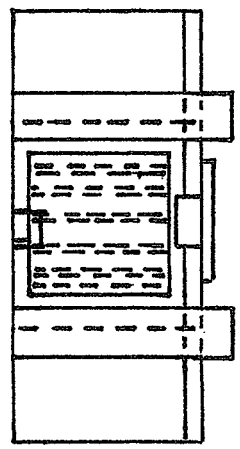
FIG. 4A is a cross-sectional view taken along line 4A-4A of FIG. 4.
Figure 4:
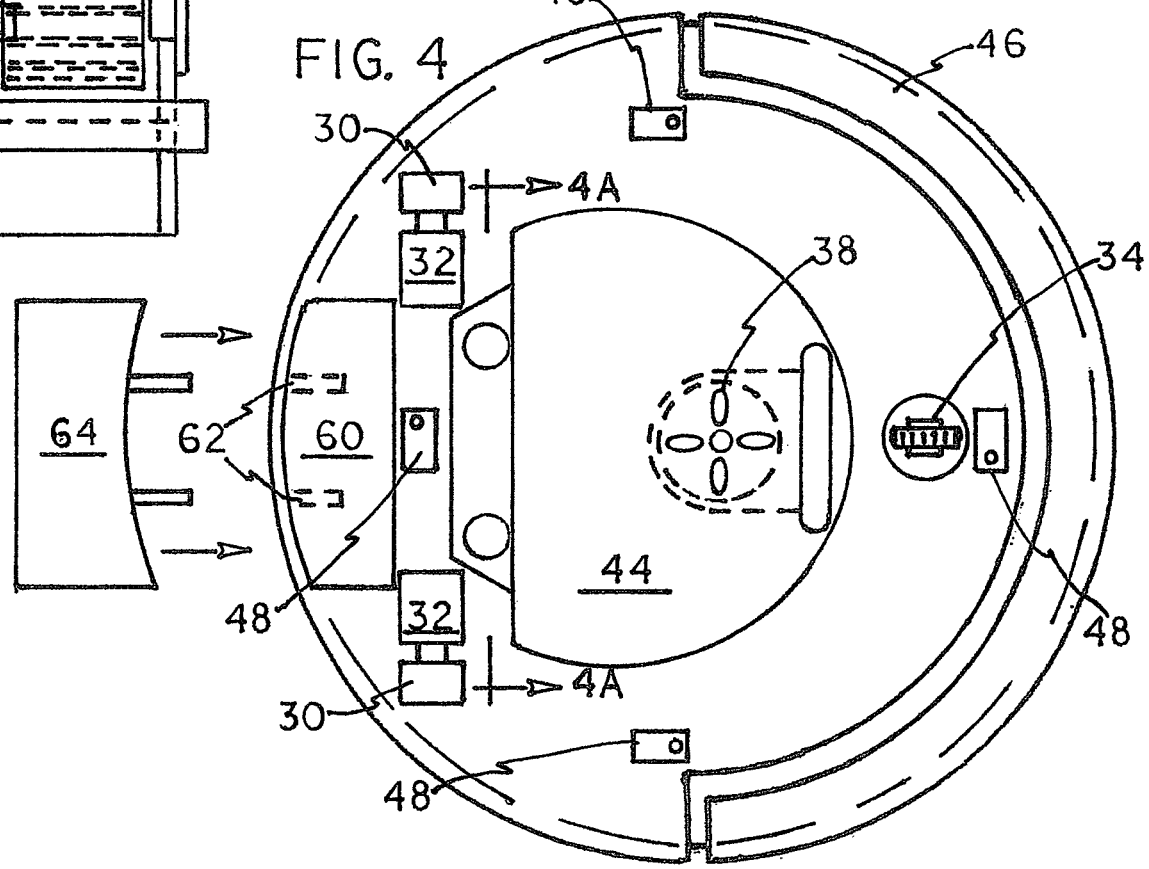
FIG. 4 is a plan view of the base assembly taken along line 4-4 of FIG. 1.
Figure 5:
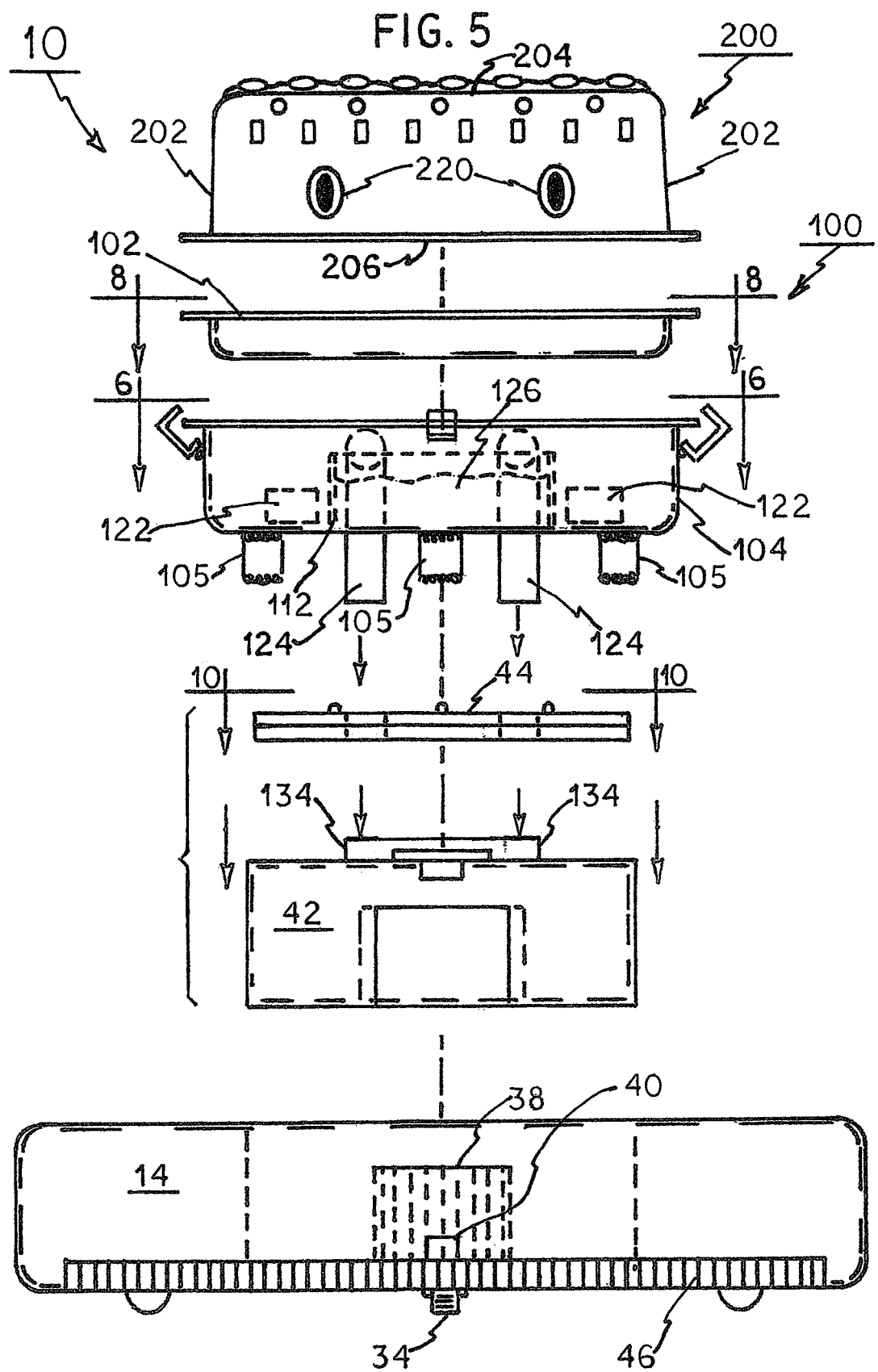
FIG. 5 an exploded front elevational view of the system.
Figure 6:
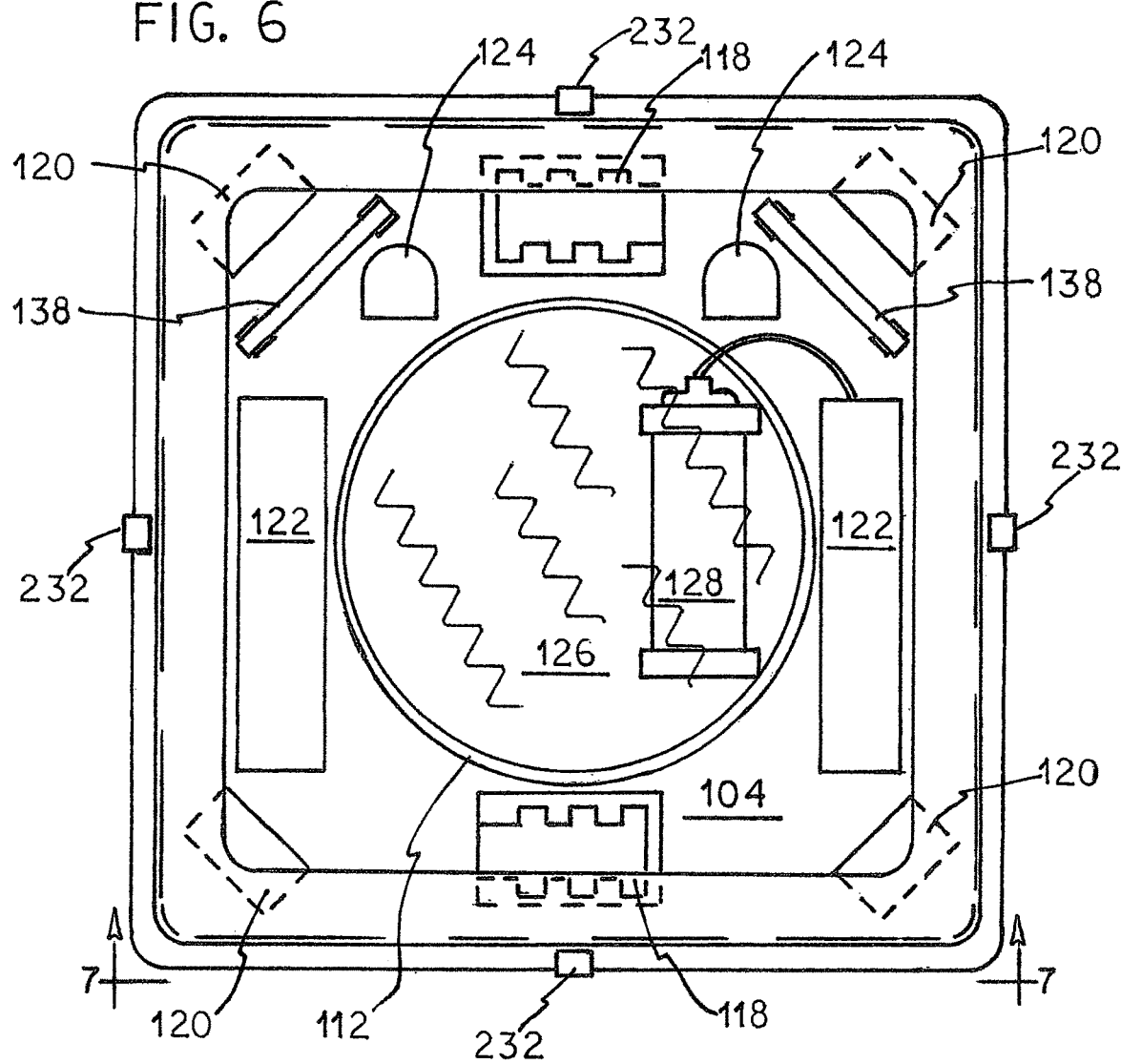
FIG. 6 is a plan view of the lower pan taken along line 6-6 of FIG. 5.
Figure 7:
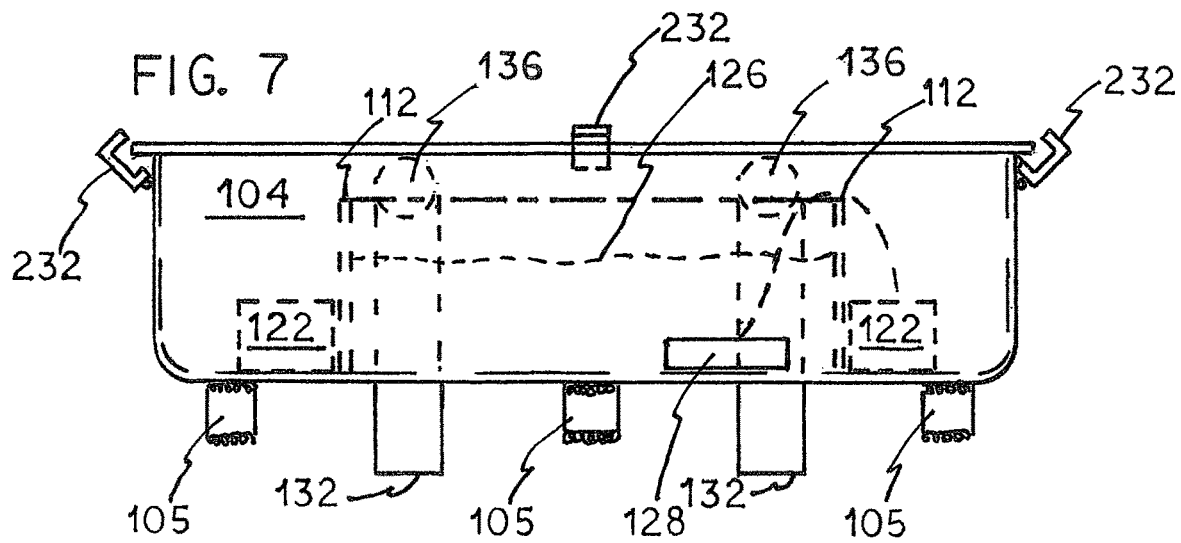
FIG. 7 is a cross sectional view taken along line 7-7 of FIG. 6.
Figure 10:
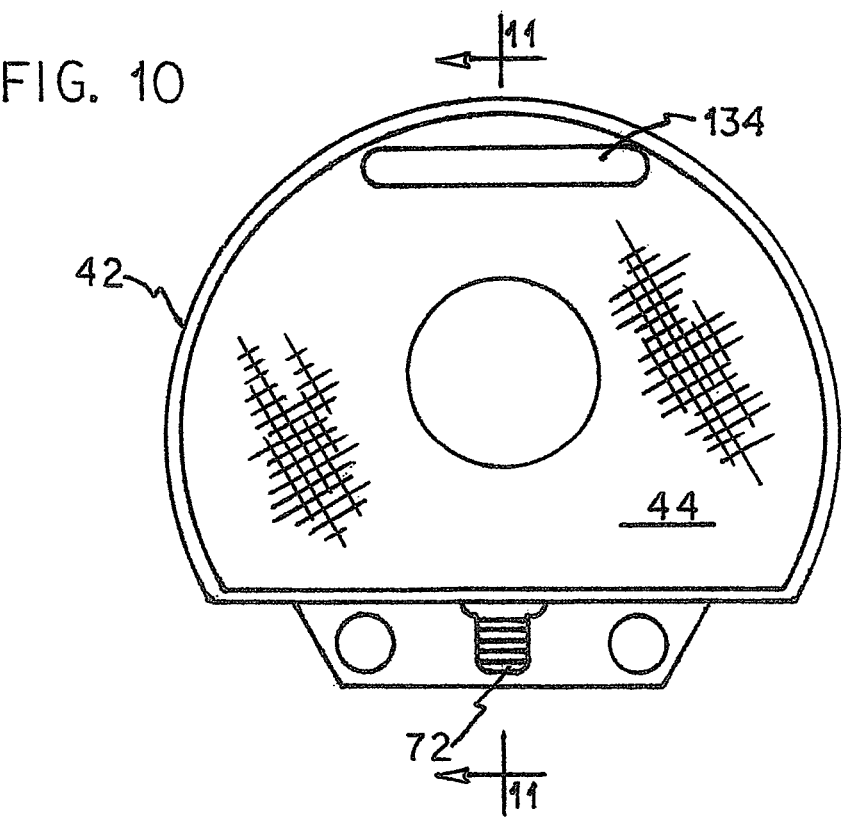
FIG. 10 is a cross sectional view of the fluid canister taken along line 10-10 of FIG. 5.
Figure 11:
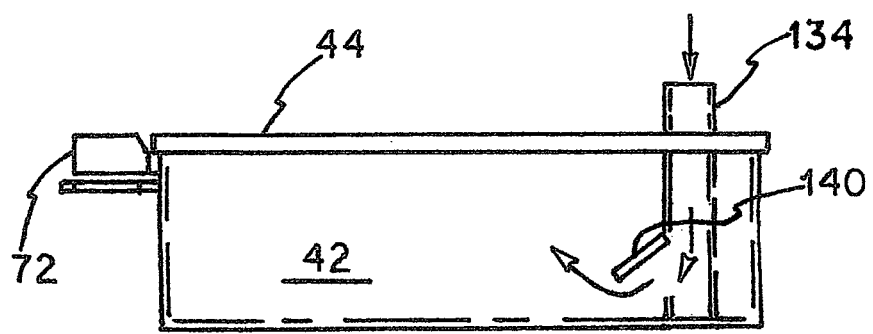
FIG. 11 is a side elevational view of system but with the cell phone removed.

With reference now to the drawings, and in particular to FIG. 1 thereof, the preferred embodiment of the new and improved bed bug detector system embodying the principles and concepts of the present invention and generally designated by the reference numeral 10 will be described.

The present invention, the sleep security method is comprised of a plurality of steps. Such steps in their broadest context include providing a bed, providing at least one sensor, providing a printer, providing a transceiver, operating coupling at least one sensor to the printer through the transceiver, and finally creating a written record. Such steps are individually configured and correlated with respect to each other so as to attain the desired objective.

From a specific viewpoint, embodiments of the invention include a bed bug detector system shown in FIGS. 1 through 11.

In the first embodiment of the bed bug detector system first provided is a base assembly 14. The base assembly has a base 16. The base has a circular floor 18 and a cylindrical side wall 20 and an open top forming a lower chamber. The base has a forward region 22, a rearward region 24, a left side region 26, and a right side region 28. The base assembly includes a fluid canister 32. The fluid canister contains water 34, a yeast pill 36, and a sugar pill 38 functioning to create carbon dioxide and to attract bed bugs. The pills are preferably in the shape of a bed bug to be attracted and killed. The base assembly includes a fluid motor 42 with a fluid fan 44 functioning to evacuate carbon dioxide from the fluid canister to attract bed bugs. A sugar jar 46 retains a supply of sugar tablets. A yeast jar 48 retains a supply of yeast tablets. For receiving and retaining bed bugs, three stacks of adhesive pads 52 are recessed on the floor of the base. Each stack includes alternating adhesive and adhesive sheets. The next component of the base assembly is a smoke/fire detector 54. For powering the components of the base assembly, the base assembly has two battery packs 56 within the lower chamber adjacent to the forward and rearward regions respectively. The battery packs are for powering the system including the smoke/fire defector and the motor of the base assembly and a recorded greeting. The base assembly includes charging ports 58. The charging ports function to recharge the battery pack.

A killing assembly 100 is next provided. The killing assembly is structurally and operatively coupled to the base assembly. The killing assembly includes an upper dish 102 and a lower dish 104. The upper dish has parallel electrically charged wires 106. The wires function to kill bed bugs coming into contact with the wires. The upper dish has a grid 108 of un-charged wires. The un-charged wires are spaced above the electrically charged wires. In this manner human contact with the electrically charged wires is abated. The killing assembly includes a plurality of adhesive sheets 110. The adhesive sheets are supported in two stacks 112, 114 laterally spaced in the lower dish to receive and retain bed bugs killed by the electrically charged wires. The electrically charged wires are optional. Each stack includes the adhesive sheets with adhesive sheets 116 between the adhesive sheets.

A plurality of heating elements 118 are provided in the lower dish functioning to attract bed bugs. The killing assembly includes a tube 124 and olfactory patches 128 positioned within the base assembly. The olfactory patches are soaked in bed bug attracting pheromones. The tube is circular in configuration and is structurally and operatively secured within the killing assembly. Apertures are provided along the length of the tube. The tube has a free end operatively coupled to the fluid canister for creating a cloud of carbon dioxide.

Next, an attracting assembly 200 is provided for attracting bed bugs to be killed. The attracting assembly is structurally and operatively coupled to the killing assembly. The attracting assembly has a frusto-conical side wall 202, an open top 204, and an open bottom 206. The attracting assembly includes peripheral components. The peripheral components are on the exterior surface of the attracting assembly. The peripheral components include heating elements 118, synthetic fur 216, adhesive patches 218, and indicia in the form of eye balls 220 creating the appearance of a creature. The eye balls are preferably made of fluorescent material for illumination to attract bed bugs. Square holes 226 are located peripherally through the attracting assembly to create a cloud around the system and in proximity thereto for attracting bed bugs to be killed. Lower clips 230 or magnets are provided on the base assembly. The clips or magnets couple the killing assembly to the base assembly. Upper clips 232 are provided on the killing assembly. The upper clips couple the attracting assembly to the killing assembly.

Next, a control assembly 300 is provided. The control assembly is structurally and operatively coupled to the attracting assembly, the killing assembly, the base assembly, and a cell phone 314. The control assembly includes a user visible digital UPC, universal product code 304. The control assembly includes a battery power percentage indicator 306. The system has an ON/OFF button 310 and a CLAP ON/CLAP OFF switch 308 for a battery power percentage indicator.

Lastly provided is the cell phone 314 with a macro-lens 316 for wide angle photography with enlargements. The cell phone is structurally and operatively coupled to the attracting assembly. A cable 328 supports the cell phone. Such cable is for cell phone support and repositioning purposes. Two light emitting diodes (332) are positioned adjacent to the macro-lens for illuminating the bed bug to be photographed. The positioning of the cell phone with its camera and the frusto-conical shape of the attracting assembly side wall, allows for the viewing of the side wall with attracted bed bugs.

Figure 12:
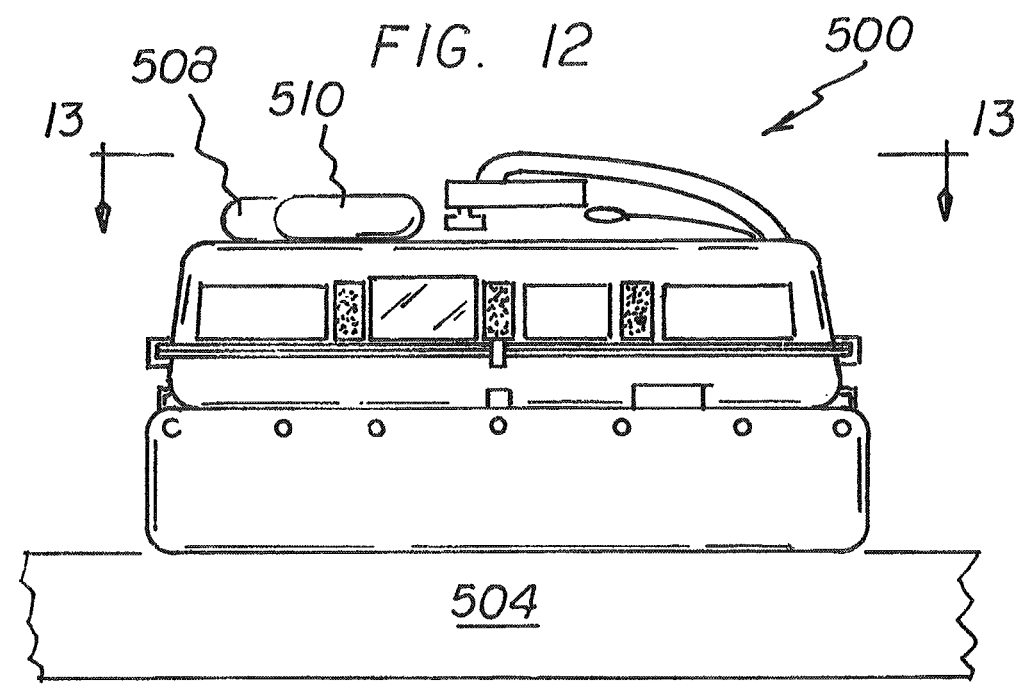
FIG. 12 is a side elevational view of a system for carrying out the sleep security method of the present invention.
Figure 13:
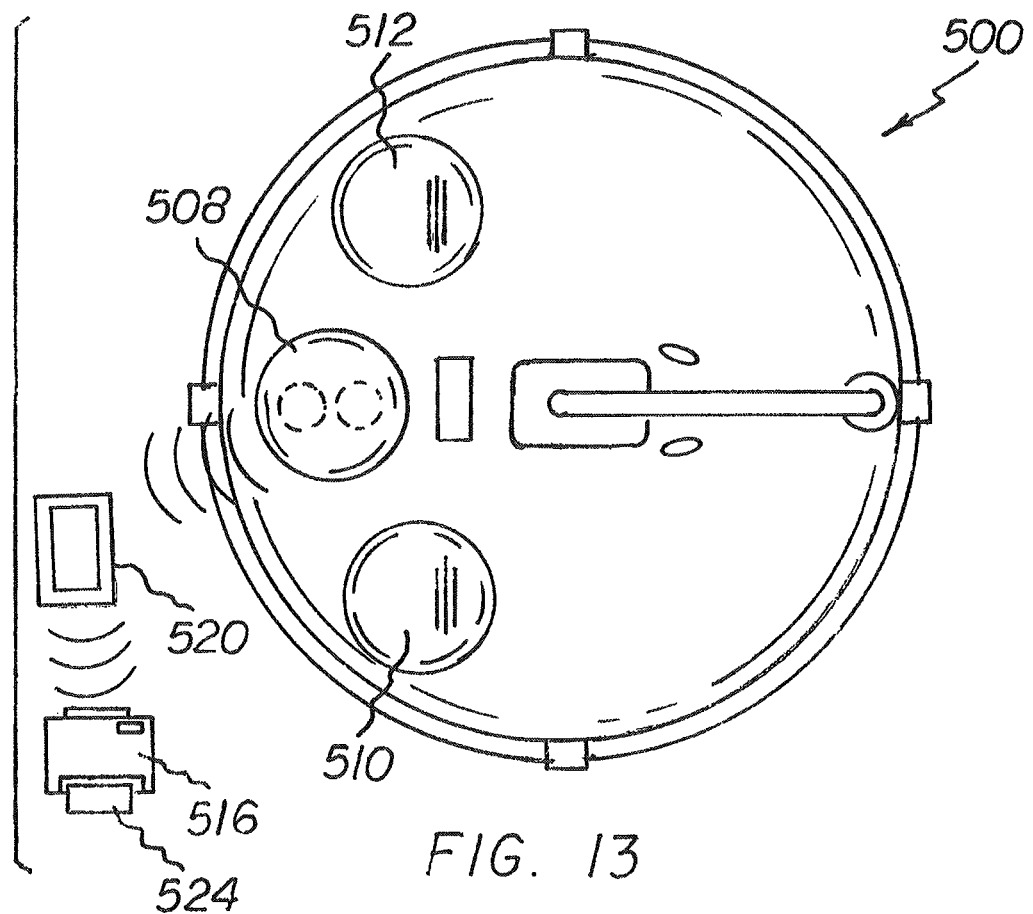
FIG. 13 is a plan view of the system taken along line 13-13 of FIG. 12.

The preferred specific method of the present invention is illustrated in FIGS. 12 and 13. The method is a sleep security method 500 for detecting favorable and unfavorable sleeping conditions and for printing out a record of such detecting. The detecting and the printing out are done in a safe, convenient, and economical manner. The method comprises a plurality of steps in combination.

The first step is providing a bed 504.

The next step is providing a plurality of sensors for the detecting of the sleeping condition and for generating a signal in response to such detecting. The plurality of sensors include a bed bug detector 508, a smoke detector 510, and a noxious gas detector, the noxious gas 512 chosen from the class including natural gas, propane, gas, and carbon monoxide. The plurality of sensors is located in operative proximity to the bed.

The next step is providing a printer 516.

The next step is providing a transceiver 520.

The next step is operatively coupling the plurality of sensors to the printer through the transceiver.

The next step is creating a written record by the printer of the detecting of a favorable sleeping condition resulting from in excess of 14 days with no detecting of a bed bug.

The final step is creating a written record 524 by the printer of the detecting of an unfavorable condition resulting from a detecting of a bed bug, smoke, or a noxious gas.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A sleep security method comprising:
   providing a bed;
   providing a plurality of sensors for the detecting of a sleeping condition and for generating a signal in response to such detecting, the plurality of sensors including a bed bug detector, a smoke detector, and anxious gas detector, the noxious gas chosen from a class including natural gas and propane gas and carbon monoxide, the plurality of sensors being located in operative proximity to the bed;
   providing a printer;
   providing a transceiver;
   operatively coupling the at least one sensor to the printer through the transceiver; and
   creating a written record by the printer of the detecting of the sleeping condition.

2. The method as set forth in claim 1 wherein the sleeping condition is a favorable condition resulting from a predetermined number of days with no detecting of a bed bug.

3. The method asset forth in claim 2 wherein the predetermined number of days is in excess of 14 days.

4. A sleep security method (500) for detecting favorable and unfavorable sleeping conditions and for printing out a record of such detecting, the detecting and the printing out being done in a safe, convenient, and economical manner, the method comprising, in combination:
   providing a bed (504);
   providing a plurality of sensors for the detecting of the sleeping condition and for generating a signal in response to such detecting, the plurality of sensors including a bed bug detector (508), a smoke detector (510), and a noxious gas detector (512), the noxious gas chosen from a class of noxious gasses including natural gas and propane gas, and carbon monoxide, the plurality of sensors being located in operative proximity to the bed;
   providing a printer (516);
   providing a transceiver (520);
   operatively coupling the plurality of sensors to the printer through the transceiver;
   creating a written record by the printer of the detecting of a favorable sleeping condition resulting from in excess of 14 days with no detecting of a bed bug; and
   creating a written record (524) by the printer of the detecting of an unfavorable condition resulting from a detecting of a bed bug, smoke, or noxious gas.

\* \* \* \* \*